United States Patent [19]

Younkes

[11] Patent Number: 5,709,663
[45] Date of Patent: Jan. 20, 1998

[54] SYRINGE INFUSION DEVICE

[76] Inventor: William E. Younkes, 4900 Preserve Pkwy. North, Greenwood Village, Colo. 80121

[21] Appl. No.: 595,881

[22] Filed: Feb. 6, 1996

[51] Int. Cl.⁶ ............................................. A61M 37/00
[52] U.S. Cl. ........................... 604/154; 604/228; 604/218
[58] Field of Search ............................. 604/154, 228, 604/232, 218, 221

[56] References Cited

U.S. PATENT DOCUMENTS

| | | | |
|---|---|---|---|
| 1,667,273 | 4/1928 | Stewart | 604/232 |
| 2,503,445 | 10/1950 | Lermer | 604/221 |
| 2,555,878 | 6/1951 | Drabicki | 604/228 |
| 3,973,554 | 8/1976 | Tipton | 604/187 |
| 3,993,063 | 11/1976 | Larrabee | 604/187 |
| 4,699,614 | 10/1987 | Glazier | 604/228 |
| 5,050,617 | 9/1991 | Columbus | 604/228 |
| 5,350,367 | 9/1994 | Stiehl | 604/228 |
| 5,405,326 | 4/1995 | Haber | 604/232 |
| 5,445,620 | 8/1995 | Haber | 604/228 |

*Primary Examiner*—Sam Rimell
*Assistant Examiner*—Luke Yeh
*Attorney, Agent, or Firm*—Davis, Graham & Stubbs LLP

[57] ABSTRACT

A device for transferring liquid between the body of a patient and a syringe includes a syringe barrel defining a bore, a plunger that may slide through the bore to force liquid into or out of the bore, and a pump capable of sliding the plunger. The pump housing positively connects to the bore by sliding a protrusion formed on the exterior of the pump housing into an indentation formed within the interior surface of the bore.

19 Claims, 2 Drawing Sheets

SYRINGE INFUSION DEVICE

FIELD OF THE INVENTION

The present invention relates to the broad field of infusion devices, and more particularly to medical syringe devices useful to transfer a selected amount of fluid between a syringe device and the body of a patient over a given time frame.

BACKGROUND OF THE INVENTION

Syringes and related devices include at a minimum a barrel with a cylinder bore and a slidably operative plunger in the bore. Liquid, generally medicine, is contained in the bore between the plunger and an opening in one of the ends of the bore. The opening is in communication with a needle, catheter or similar instrument which is inserted either subcutaneously or intravenously into the body of a patient. The plunger is slid towards the opening so as to force the medicine out of the barrel and into the body of the patient through the needle or catheter.

Traditionally, syringes have been manually controlled by an operator who slides the plunger towards the opening. This technique is effective and still used to rapidly introduce medicine into a patient. However, it is often desirable to inject medicine into the patient at a relatively slow rate over a period of time. For instance, some types of chemotherapy programs and some types of blood clotting treatments used before or after surgery require a controlled, gradual introduction of medicine into the patient. Pharmokinetic variations require different injection rates for different medicines; the patient may be seriously injured if the medicine is injected too quickly, and the medicine may not be fully effective if the medicine is not injected quickly enough. Attaching a machine controlled pump that drives the plunger—typically called an infusion pump—provides an improvement over manual operation. Several problems with controlled infusion devices remain.

The first controlled infusion devices were designed to be used in hospitals or other clinical environments, where trained personnel were present to operate the devices. Improvements in pump drivers and safer and more efficacious medicines now allow controlled infusion to be performed at a patient's home or other non-clinical location, and to be performed directly by the patient without any expert supervision. While this is more convenient and less expensive for the patient, current systems have not been adequately simplified for optimum self use. In particular, current devices are rather bulky, and may be difficult to operate by patients who are often enervated by the malady for which they are receiving medical treatment. The interconnections between the syringe barrel, plunger, and pump may be complicated and difficult to secure by patients who generally receive only limited training in the operation of an infusion device. Also, cleaning the infusion devices may cause substantial difficulties. In the known infusion devices, the syringe barrel is mounted to the plunger pump through coupling some form of protrusions on the exterior surface of the syringe barrel with some form of receptacles on an inside surface of the pump. Cleaning these receptacles presents difficulties because of the inherent difficulties of removing waste material from an indented surface. Yet, it is essential to keep the pump clean and sterile, or else the medicine in the syringe could become contaminated. The syringe barrels generally are prepackaged with medicine and are designed to be discarded after each use, hence cleaning the syringe barrels is unnecessary.

U.S. Pat. No. 4,931,041 issued Jun. 5, 1990 discloses an infusion syringe pump with a position locator, so that the delivery of medicine may be carefully controlled. However, the device does not provide for any positive connection between the device's plunger and syringe barrel, which would make home use by an untrained user difficult or impossible. U.S. Pat. No. 3,993,065 issued Nov. 23, 1976 to Szabo et al. discloses a fluid infusion device that uses the traditional connection method between the pump and syringe barrel of connecting the pump to the outside of the barrel. As mentioned above, this arrangement causes several problems, such as the difficulty of cleaning the pump housing. A syringe injector with a similar connection between the pump and the syringe barrel is disclosed in U.S. Pat. No. 4,634,431 issued Jan. 6, 1987 to Whitney et al. U.S. Pat. No. 5,370,621 issued Dec. 6, 1994 to Godat et al. discloses a syringe barrel with interior indentations that support a plunger stopper. However, no mechanism is provided for attaching a plunger driver to these recesses; the device merely terminates at an open end. Thus, the problem of connecting a syringe barrel and pump to solve the above described problems has heretofore remained unsolved.

SUMMARY OF THE INVENTION

The present invention provides for an improved infusion device including a syringe barrel, plunger, and plunger pump and housing.

Protruding tabs on the pump housing fit and lock into corresponding receptacles formed into the interior of the syringe barrel. The syringe barrel is preferably a cylinder of a constant cross section, with a proximal end and a distal end. A bore, also preferably cylindrical, exists within the interior of the syringe barrel. The bore narrows at its distal end towards an opening at the extreme distal end of the bore. A needle, catheter, or similar fluid transfer device may be attached to the barrel at the distal bore opening so that the bore may be brought into fluid communication with the body of patient. A fluid that is intended to be injected into the patient, such as medicine, is placed into the syringe. Preferably, the medicine is placed into the syringe at a sterile facility and supplied to the ultimate user of the syringe in a sterile condition.

The driving motion of the pump may be accomplished in numerous ways known in the art, such as by a worm gear or other mechanism. The pump housing contains a mating section that fits into the bore. Protrusions on the mating section fit within receiving indentations formed into the bore.

The receiving indentations are aligned with the bore axis for a distance, so that the mating section may be slid into the bore. The receiving indentations are formed to provide a positive connection between the protrusions and the receiving indentations. The positive connection may be achieved in several ways. One method is to provide an irregularity in the cross section of the indentations, such by placing a restriction in the indentations so that the cross section of the indentation is larger proximal and distal to the restriction. The extreme distal indentation sections preferably are formed into the same shape as the protrusions. The protrusions of the distal mating section may then be forced through the indentation restrictions, and will snap into place after passing the restrictions.

Another way to achieve a positive connection between the indentations and protrusions is to form the indentations with a tangential leg at their distal sections. After the pump housing is fully inserted into the syringe barrel, it may then be twisted to place the protrusions into the tangential legs. The tangential legs may contain an irregularity so that the pump housing will snap into place when the cap is twisted, in the manner of a bayonet lug attachment.

It should be apparent that the mating section of the pump housing cannot be inserted into the syringe bore unless the protrusions are aligned with the indentations. Thus, the pump housing cannot be improperly mated with the barrel. As both the protrusions and indentations are visible (before mating has been accomplished, or even after mating has been accomplished if the syringe barrel is transparent), a user of the device may easily align the pump housing and the barrel. Also, wings may be formed on the exterior of the syringe barrel in a position corresponding to the indentations, to further assist the user in gripping and aligning the device. The protrusions, indentations, and wings provide tactile sensation, so that even visually impaired user may connect the pump housing and the barrel.

The mating section of the pump connects to the remainder of the pump housing, which has a larger cross section than the mating section. The transition between the mating section and the remainder occurs at an annular ridge in the pump housing, so that the annular ridge abuts the proximal edge of the syringe barrel when the mating section of the pump housing is fully inserted into the barrel. This contact between the pump housing and syringe barrel strengthens the connection therebetween and provides a user with visual confirmation that the connection is secure. Since the connection between the pump housing and the syringe barrel is made through this annular ridge and through the longitudinal protrusion/indentation fit, no additional connectors need extend radially away from the device, and its profile is thus minimized.

A plunger extends longitudinally out of the mating portion of the pump housing and fits into the syringe bore. The plunger is preferably elastomeric and has a circumference that is slightly larger than the bore circumference, so that placing the plunger into the bore prevents fluid communication past the plunger. The plunger may be moved distally from the mating portion through the bore by the pump. The distal motion of the plunger applies pressure to the fluid and forces it through the bore opening. After the device has been used to introduce fluid into the body of the patient, the pump housing and syringe barrel may be detached from one another by reversing the connection procedure. Typically, the syringe barrel is then discarded. To avoid contamination, the pump housing must be cleaned and sterilized before it is used with another syringe barrel. This is easy to do, as the pump housing exterior contains no recessed surfaces.

While the above description has assumed that the syringe is used to introduce fluid into the body of a patient, it should be appreciated that the syringe could also be used aspirate fluid from the patient. The syringe bore would be initially devoid of fluid, and the plunger would then be moved proximally instead of distally, so as to create negative pressure in the cylinder bore. The above described advantages of the invention are equally applicable to fluid withdrawal as to fluid introduction.

The present invention provides an infusion device having a slim profile, since the pump housing and syringe barrel may slide into each other. The interconnection between the syringe barrel, plunger, and pump housing may be easily formed by a patient with minimal training, and may be visually verified by the patient. Also, the pump housing may be easily cleaned and sterilized between fluid transfer sessions.

DETAILED DESCRIPTION OF THE INVENTION

Figure 1:
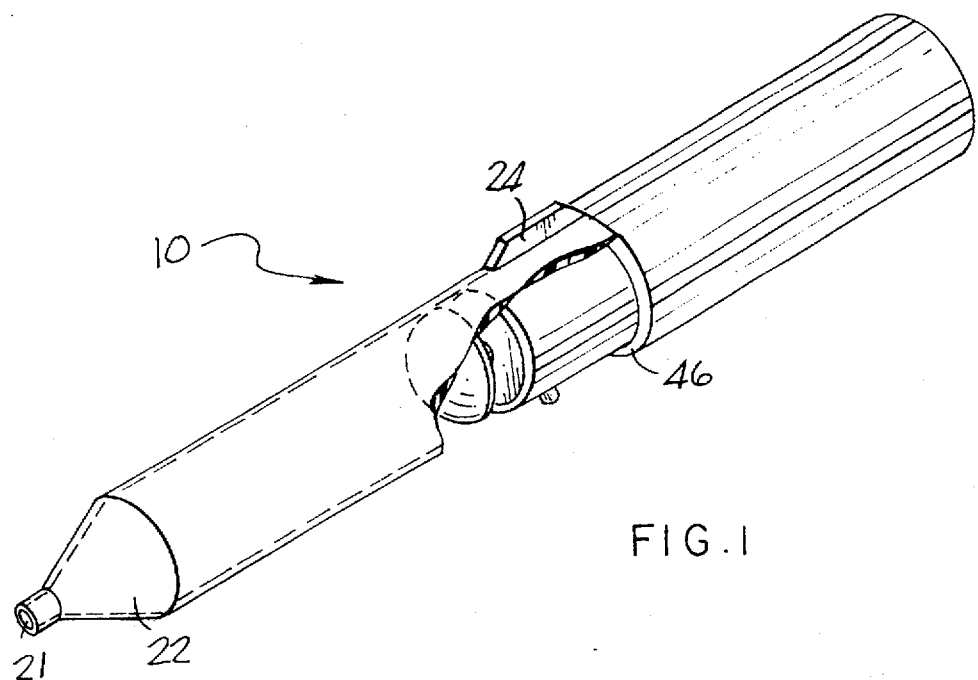
FIG. 1 is a perspective view of an apparatus embodying the present invention, with portions cut away.
Figure 1A:
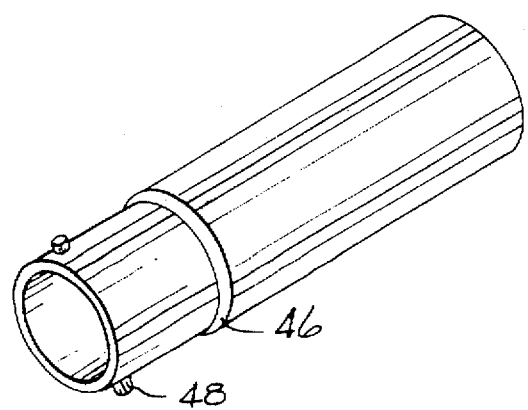
FIG. 1A is a perspective view of the pump housing of FIG. 1, shown by itself.
Figure 1B:
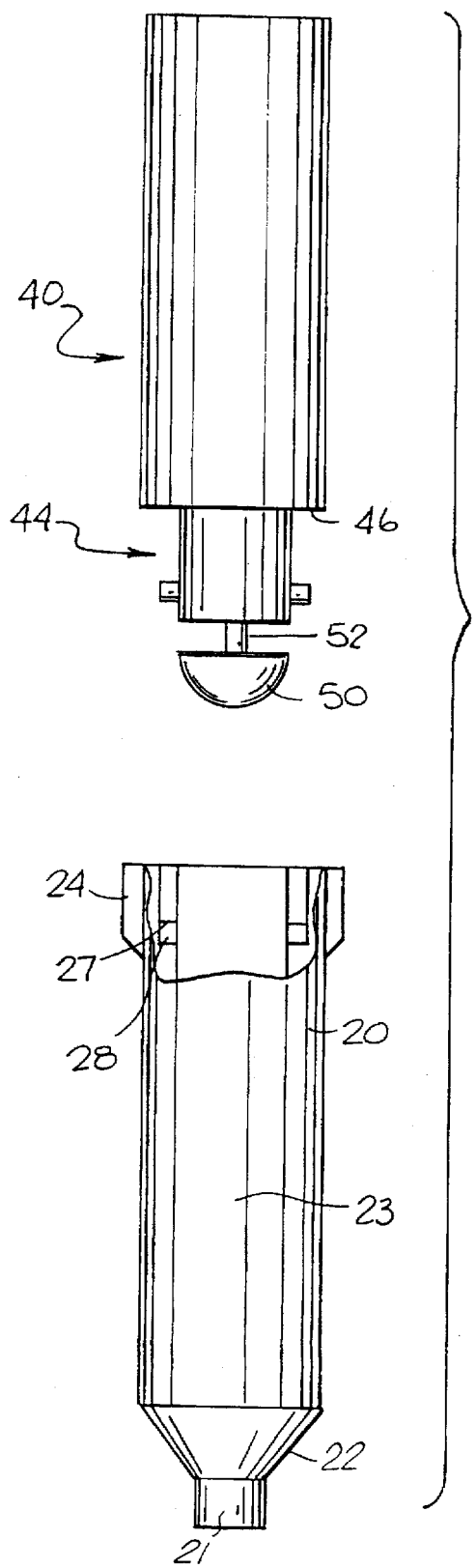
FIG. 1B is a side elevational of FIG. 1, before the pump housing is inserted into the syringe barrel.

With reference to FIG. 1 and FIG. 1B, the fluid injection device 10 includes a syringe barrel 20 with a distal end and a proximal end with a bore 23 formed therein extending from the distal to the proximal end. An opening 21 in the distal end of the bore 23 provides fluid communication between the bore 23 and the exterior of the syringe barrel 20. Preferably, the syringe barrel contains a tapered section 22, where the cross section is reduced near the opening 21. The bore 23 is thus also reduced in cross section near the opening 21. A needle, catheter, or other fluid transfer device (not shown) may be fitted onto the opening 21 to transfer fluid between the body of a patient and the bore 23 of the device 10.

A pump housing 40 attaches to the proximal end of the syringe barrel 20. The pump housing contains a plunger 50 attached to a plunger rod 52 and drive means to advance and retract the plunger 50 through the bore 23. The plunger 50 is preferably elastomeric and is dimensioned so that it must be slightly compressed to fit within the bore 23, so that the plunger 50 and bore 23 form a fluid seal, in the manner known in the art.

Figure 2:
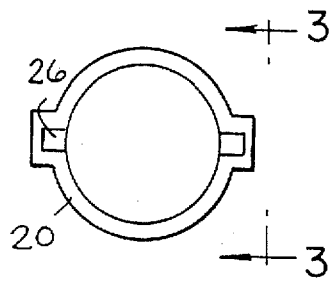
FIG. 2 is a top view of the view of the syringe barrel of FIG. 1.
Figure 3:
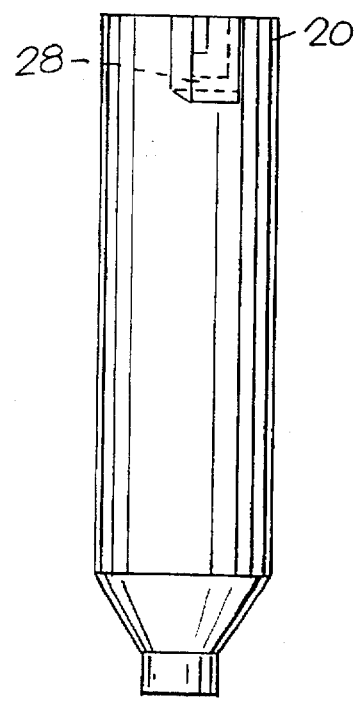
FIG. 3 is a cross sectional view taken along line III—III in FIG. 2.

The pump housing 40 includes a mating section 44 at the distal end of the pump housing 40; the mating section 44 may be received within the bore 23 (see FIG. 1A). The mating section is sized to fit snugly within the bore 23. A protrusion 48 extends radially outward from the primary surface of the mating section 44. An indentation 26 is arranged in the bore to receive the protrusion 48. The indentation is arranged primarily longitudinally along the bore 23, so that the mating section 44 may be slid into the syringe barrel 20. The indentation 26 may be seen in cross section in FIG. 1B, and from a top view in FIG. 2. In a preferred embodiment, the indentation 26 is formed in a wing 24 that protrudes from the exterior surface of the syringe barrel 20. The wing 24 provides additional thickness in the syringe barrel 23 to reinforce the syringe barrel 23 at the indentation 26 location. The wing 24 also serves as a handle so that a user of the device 10 may easily grasp the syringe barrel 20. The wing serves a third function of easily informing the device 10 user of the location of the indentation 26, which is particularly useful to the visually impaired, who can locate the wing 24 by touch.

The preferred embodiment has a total of two protrusions such as protrusion 48, two corresponding indentations such as indentation 26, and two corresponding wings such as wing 24, spaced evenly around the pump housing 40 or syringe barrel 20. However, the device could have only one protrusion/indentation pair or could have more than two. Also the indentation 26 could be formed directly in the device barrel 23 without the use of the wing 24.

The indentation 26 is formed to provide for a positive connection with the protrusion 48 when the mating section 44 is fully inserted into the syringe barrel 21. This may be achieved by an irregularity 27 in the surface in the indentation directly proximal to an indentation locking position 28, at the extreme distal end of the indentation 26 (see FIG. 2). The irregularity 27 is a restriction in the indentation cross section, so that the protrusion 48 must be forced through the irregularity 27. The indentation locking position 28 is contoured to the shape of the protrusion 48, so that the protrusion 48 will lock into place once it is forced through the irregularity 27. Preferably, the locking portion 28 is tangentially offset from the remainder of the indentation 26 (see FIG. 4), so that relative rotational motion must be applied between the syringe barrel 20 and the pump housing 40 to secure the connection. While a user may easily apply the rotational motion to secure the connection, it is unlikely that inadvertent contact will reverse the rotational motion.

The connection between the pump housing 40 and the syringe barrel 20 is further secured by an annular ridge 46 that separates the mating section 44 from the remainder of the pump housing 40. When the protrusion 48 is fitted into the locking section 28 of the indentation 26, the annular ridge 46 abuts against the proximal edge of the syringe barrel 20 and thus shares in any compressive fore between the pump housing 40 and the syringe barrel 20.

Aside from improving the connection between the pump housing 40 and the barrel 20, the annular ridge 46 serves as a visual and tactile indicator of when the connection is complete. If there is any gap between the pump housing 40 and the syringe barrel 20, the device 10 user is made aware that the connection is not complete, and that the pump housing 40 must be further inserted into the barrel 20.

After the pump housing 40 is connected to the syringe barrel 20, fluid may be injected into or aspirated from the body of a patient. Injection or aspiration is accomplished by sliding the plunger 50 through the bore 23. The plunger 50 is connected by the plunger rod 52 to a suitable drive means, such as a worm gear contained in the pump housing 40, as is well known in the art.

After the device 10 has been used, the pump housing 40 is separated from the syringe barrel 20 by reversing the connection procedure. That is, force is applied to the pump housing 40 to remove the protrusion 46 form the locking position 28, across the irregularity 27, and through the longitudinal portion of the indentation 26. Once separated form the syringe barrel 20, the mating portion 20 of the pump housing 40 must be cleaned before it is again used. This is easily done, as the mating portion consists of a smooth surface and the protrusion 48. No indentations are on the mating portion 40 to collect the syringe fluid or other potential contaminants. While the indentation 26 in the syringe barrel 20 likely will collect contaminants, this is not in general a problem because the syringe barrel 20 is preferably disposable.

What is claimed is:

1. An infusion device comprising:
   an elongated syringe barrel with a proximal end and a distal end with a bore therebetween,
   a syringe plunger that may slide through at least a portion of the bore, sealingly engaged with the barrel to drive fluid out the distal end upon sliding the plunger toward the distal end;
   a pump operatively engaged with the plunger to slide the plunger through the bore;
   a pump housing containing the pump, the pump housing including a mating portion and a non-mating portion, the mating portion extending from the non-mating portion; and
   the mating portion of the pump housing including means for rotatably and releasably attaching to the syringe barrel with the bore.

2. The infusion device of claim 1, wherein the mating portion of the pump housing is slidably received within the bore, and the non-mating portion remains exterior to the bore.

3. The infusion device of claim 2, wherein an indentation is formed within the bore, a protrusion protrudes from the mating portion of the pump housing, and the protrusion is receivable within the indentation.

4. The infusion device of claim 3, wherein the syringe barrel includes a wing extending radially away from the barrel, and an indentation is substantially radially aligned with at least one wing.

5. The infusion device of claim 3, wherein the bore indentation includes means for locking into the pump housing protrusion after the portion of the pump housing that is slidably received within the bore has been slid into the bore.

6. The infusion device of claim 5, wherein the means for locking the bore indentation into the pump housing is provided by a narrowing in the indentation and a receptacle formed in the indentation adjacent the narrowing adapted to the shape of the protrusion.

7. The infusion device of claim 6, wherein the receptacle is tangentially offset from the remainder of the indentation.

8. The infusion device of claim 1, wherein the mating portion of the pump housing being rotatably and releasably attachable to the syringe barrel, is by a set of threads and mating threads within the syringe barrel and on the mating portion of the pump housing.

9. The infusion device of claim 8, wherein said threads and mating threads are substantially continuous.

10. The infusion device of claim 8, wherein said threads and mating threads are intermittent.

11. The infusion device of claim 10, wherein said threads and mating threads are a bayonet attachment.

12. A method of transferring fluid between a syringe and a body, comprising:
   placing a syringe barrel in fluid communication with the body, the barrel defining a bore there-within;
   placing a syringe plunger within the bore, the plunger being slidable therethrough and sealingly engaged with the barrel to drive fluid out the bore upon sliding the plunger through the bore;
   rotatably attaching a pump housing to the interior of the bore, the housing containing a pump operatively engaged with the plunger; and
   sliding the plunger through the bore to drive fluid out the bore and into the body.

13. The method of claim 12, wherein the step of attaching the pump housing to the interior of the bore further comprises: sliding a protrusion on the exterior of the pump housing into an indentation formed into the bore.

14. The method of claim 13, including the additional steps of:
   removing the syringe barrel from fluid communication with the body and removing the pump housing from the interior of the bore.

15. The method of claim 14, including the additional steps of:
   cleaning the exterior surface of the pump housing and attaching the pump housing to a new syringe.

16. The method of claim 12, wherein said step of rotatably attaching a pump housing to the interior of the bore includes threading together a set of threads and mating threads in the bore and on the pump housing.

17. The method of claim 16, wherein said threads and mating threads are substantially continuous.

18. The method of claim 17, wherein said threads and mating threads are intermittent.

19. The method of claim 18, wherein said threads and mating threads are a bayonet attachment.

* * * * *